(12) United States Patent
Doorschodt

(10) Patent No.: US 8,993,225 B2
(45) Date of Patent: Mar. 31, 2015

(54) DEVICE FOR TRANSPORTING AN ORGAN

(75) Inventor: Benedict Marie Doorschodt, Amsterdam (NL)

(73) Assignee: Oxiplenish B.V., Amsterdam Zuidoost (NL)

( * ) Notice: Subject to any disclaimer, the term of this patent is extended or adjusted under 35 U.S.C. 154(b) by 1669 days.

(21) Appl. No.: 11/918,843

(22) PCT Filed: Apr. 24, 2006

(86) PCT No.: PCT/NL2006/050098
§ 371 (c)(1),
(2), (4) Date: Oct. 19, 2007

(87) PCT Pub. No.: WO2006/112720
PCT Pub. Date: Oct. 26, 2006

(65) Prior Publication Data
US 2010/0015592 A1    Jan. 21, 2010

(30) Foreign Application Priority Data
Apr. 22, 2005   (NL) .................................... 1028848

(51) Int. Cl.
*A01N 1/02*    (2006.01)
(52) U.S. Cl.
CPC ............... *A01N 1/02* (2013.01); *A01N 1/0247* (2013.01)
USPC ....................................... 435/1.2; 435/284.1
(58) Field of Classification Search
CPC ..... A01N 1/02; A01N 1/0205; A01N 1/0247; A01N 1/0273; A01N 1/0263; A01N 1/021
USPC .................................................. 435/1.2, 284.1
See application file for complete search history.

(56) References Cited

U.S. PATENT DOCUMENTS

| | | | | |
|---|---|---|---|---|
| 3,843,455 A | * | 10/1974 | Bier | ............................ 435/284.1 |
| 3,877,843 A | | 4/1975 | Fischel | |
| 3,914,954 A | | 10/1975 | Doerig | |
| 5,338,662 A | * | 8/1994 | Sadri | ............................ 435/284.1 |
| 5,356,771 A | | 10/1994 | O'Dell | |

FOREIGN PATENT DOCUMENTS

| | | |
|---|---|---|
| CN | 1543785 A | 11/2004 |
| NL | 1013524 | 5/2001 |
| WO | 01/33959 A2 | 5/2001 |

OTHER PUBLICATIONS

State Intellectual Property Office of the People's Republic of China, First Office Action, Sep. 15, 2010.

* cited by examiner

*Primary Examiner* — Michael Hobbs
(74) *Attorney, Agent, or Firm* — The Webb Law Firm

(57) ABSTRACT

The invention relates to a device for transporting an organ having a container for organs, a gas-driven pump connected to the container and conduits for circulating a liquid and/or gas through the container, and a controller for controlling the pump. There is a pressure sensor in the liquid output conduit of the pump that is connected to the controller and control the drive for the pump. The invention also relates to a method for transporting an organ in a container.

14 Claims, 4 Drawing Sheets

DEVICE FOR TRANSPORTING AN ORGAN

BACKGROUND OF THE INVENTION

1) Field of the Invention

The invention relates to a device for transporting an organ, having a container for organs, a gas-driven pump connected to the container and conduits for circulating a liquid and/or gas through the container, and an attachment for a gas bottle and a gas conduit connecting the gas bottle to the pump. A first valve is provided in the gas conduit and a controller controlling said gas conduit for producing a pulsating gas flow to said pump for operation thereof is provided.

2) Description of Related Art

Perfusion of a donor organ with liquid or gas during the transport phase appreciably improves the quality of the donor organ. This appreciably reduces the risk of the receiving patient's body rejecting me donor organ, achieving for the patient a reduction in the quantity of medicines he/she will have to take to suppress rejection phenomena. Apart from the fact that this is of great importance for the patient's health, it is also of social importance, since there is a shortage of donor organs.

NL 1013524 discloses a device for mechanical organ perfusion during the transport phase of a donor organ. This device has the disadvantage that during the transport phase the pressure of the perfusion liquid in the donor organ is not accurately controlled. Because of this there is a high risk that pressure changes arise to such an extent that the organ perfusion does not proceed as it should. During the transport phase there are many factors which can lead to these pressure changes. A number of frequently occurring factors are a change in the ambient temperature, the reduction in the gas pressure as the gas container becomes emptier and the various positions in which the device is situated. As a result of this, it is with the known device during the transport phase at one moment it is possible for the situation to arise that because the liquid pressure is too low the desired organ perfusion is not achieved and at another moment, which is often worse, that because the liquid pressure is too high the donor organ becomes irreparably damaged. In addition, the known device has a too high gas consumption. As a result of this it regularly happens, and in particular in the event of unexpected delays, that during the transport phase the organ perfusion stops because the gas has run out. Since the device is intended for transport, coupling the device to a larger gas container is not a satisfactory solution.

SUMMARY OF THE INVENTION

An objective of the invention is to provide a device in which the perfusion process for the donor organ is accurately controlled. The aim is achieved with the device according to the invention, which is characterised in that there are pressure sensor means in the output conduit of the pomp, which pressure sensor means are connected to said controller and control the drive for said pump. As a result of this the controller adapts the drive for the pump whenever a pressure which does not match the desired pressure is registered in the output conduit by the pressure sensor means. In this way the perfusion process for the donor organ is accurately controlled. The gas consumption of the device is also reduced by this accurate control.

In one embodiment of the invention the device has a second valve provided in the gas conduit upstream of the first valve for controlling the pressure at said first valve. To reduce costs, use is preferably made of standard, commercially available gas containers. Whether or not use is made of a reduction valve fixed on the gas container, these gas containers can deliver a minimum pressure of about 1.5-4 bar. This minimum gas pressure delivered by the gas container is too high for it to be used to pump perfusion liquid or gas to the donor organ, since this will consequently be damaged. With the aid of a second valve, which reduces the gas pressure in the gas conduit between the gas container and the pump to a desired value, preferably between 100 and 250 mbar, these gas containers available as standard can be used for the drive for the pump. This second valve can be an on/off valve, which has an opening and closing time of about 5 ms and remains open for between 5 and 500 ms, or a reduction valve.

In one embodiment of the invention the second valve is electrically adjustable and electrically connected to said controller. As a result of this, the second valve can be controlled by the controller in such a way that in the various circumstances during the transport phase a constant average pressure is achieved in the gas conduit between the gas container and the pump. A fluctuating average gas pressure results in undesired fluctuations of the maximum pressure in the output conduit. A constant average gas pressure contributes to achieving accurate control of the perfusion process for the donor organ.

In one embodiment of the invention said pump comprises a membrane pump. A membrane pump is very suitable for pulsating pumping of perfusion liquid or gas, driven by a gas under pressure. Because of the low resistance of the membrane, the pump has a high yield. The gas containers available as standard have a capacity of 1.2 or 5 liter. As the device is intended for transport, use of a gas container of 5 liters is not desirable. Such a high yield of the pump is necessary to maintain the organ perfusion with a 1- or 2-liter gas container for the whole of the transport phase, which lasts a maximum of 60 hours. Use is preferably made of a 2-liter carbonate aluminium gas container with a gas therein at an initial pressure of 200-300 bar. These gas containers are also often used in aircraft.

In one embodiment of the invention said pump comprises a sensor for switching off said pump. This acts as a safety device in a situation where perfusion liquid is being used. It is therefore of great importance for the quality of the donor organ that only perfusion liquid, and therefore no gas bubbles, are pumped through the donor organ. The sensor registers whether there is sufficient liquid in the pump to meet this condition.

In one embodiment of the invention a buffer tank is provided between the outlet of the pump and the container.

Conducting perfusion liquid through a buffer tank by means of a gas-permeable hose (for example a semi-permeable hose which comprises the material silicone) before it reaches the container enables the perfusion liquid to absorb the matter present in the buffer tank, such as an oxygen-containing gas.

In one embodiment the device according to the invention is provided with a bottom surface, side walls and a cover, dimensioned in such a way that, when the device is placed on said cover, said device tilts towards one of said side walls. The risk of the organ perfusion not proceeding as it should is greatest when the device is in the position in which the container has been placed on the cover. Dimensioning the container such that in said position it tilts towards one of the side walls increases the chance that good organ perfusion is produced during the transport phase.

According to the invention, transporting an organ in a container comprises placing an organ in said container, closing said container and pumping a perfusion liquid as well as an oxygen-containing gas into said container, said pumping of liquid being caused by pressure from said oxygen-containing gas, the gas pressure on a pump provided thereto being varied to obtain the pumping effect and the supply of gas to said pump being determined by the liquid characteristics generated by said pump in said liquid. In this respect it is also possible that the variation of the gas pressure comprises influencing the switching on and switching off of the gas supply and/or that the variation of the gas pressure comprises influencing the gas pressure in the gas supply to said pump.

The organ to be transported is connected to the perfusion supply of the device. After the perfusion process has started the perfusion liquid or gas is pumped through the organ and then flows out of the organ into the container. If perfusion liquid is used, the organ is in direct contact with the perfusion liquid present in the container. In the situation where the organ to be transported is a kidney, the kidney is connected to the perfusion supply of the device by an artery. The desired maximum perfusion pressure is then set. The pressure of the perfusion process is controlled by controlling the supply of gas to the pump. If perfusion liquid is used, an average of 100-200 milliliter/minute will be pumped to the kidney.

In the situation where the donor organ to be transported is a liver, the perfusion supply of the device is divided into two separate perfusion supplies. One of the perfusion supplies is directly connected to the artery of the liver. The other perfusion supply contains a buffer tank. This buffer tank eliminates the pulsating perfusion pressure and a constant supply of perfusion liquid or gas arises. This perfusion supply is connected to a vein of the liver which is not an artery. In this way a pulsating and continuous perfusion supply is achieved in the artery and the vein of the liver, respectively. This situation matches the situation in which a liver is found in the human body. In the situation where perfusion liquid is used, on average 20% of the perfusion liquid pumped to the liver flows through the perfusion supply for the artery and 80% through the perfusion supply the vein. Therefore in total on average 250 milliliter/minute are pumped to the liver. Before the perfusion process for the liver starts, the desired pressure and flow of liquid are set. The quantity of perfusion liquid or gas pumped to the liver is determined by controlling the throughput of gas to the pump. Because it is known how much liquid or gas the pump pumps per pump cycle, it is possible to determine how often the pump cycle needs to be repeated per time unit to achieve the desired flow rate. A maximum perfusion pressure can also be set to prevent damage to the liver.

BRIEF DESCRIPTION OF THE DRAWINGS

The invention will be explained in more detail with reference to the drawings, in which.

DETAILED DESCRIPTION OF THE INVENTION

Figure 1:
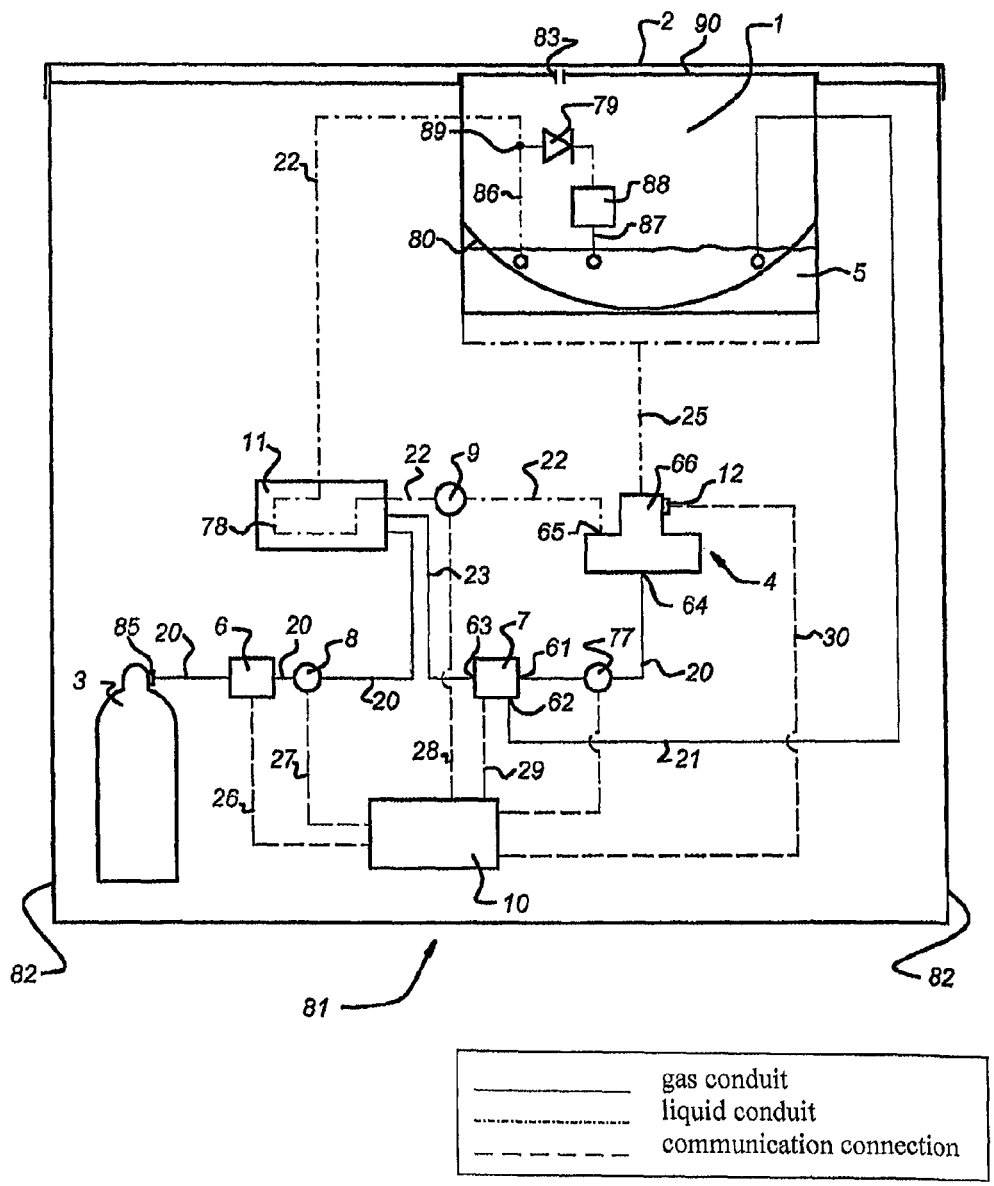
FIG. 1 shows schematically an embodiment of the device according to the invention.

FIG. 1 shows the device according to the invention in the situation where perfusion liquid 5 is used. This device comprises an organ container 1 for containing a donor organ, a membrane pump 4 for transporting the perfusion liquid 5 which can be accommodated in the organ container 1. The device further comprises a base surface 81, side walls 82 and a cover 2. The organ container 1 has a second cover 90 with a pressure relief valve 83. Said overpressure can be made semipermeable so that only gases can escape and, even if the container 1 is wrongly positioned, no liquid can escape. The pump 4 is driven by a gas under pressure from a gas container 3. The membrane pump 4 has an inlet and outlet 64 for gas and a first and second liquid connection 66 and 65. The membrane pump 4 is connected to the gas container 3 by means of a first gas conduit 20 by inlet and outlet 64. The gas container 3 has a first reduction valve 85 for reducing the gas pressure to about 1.5 bar. For the supply of perfusion liquid 5 a third liquid conduit 25 connects the first liquid connection 66 of the membrane pump 4 to the organ container 1. The third liquid conduit 25 extracts perfusion liquid 5 from two edges of the organ container 1. Because of this the third liquid conduit 25 will also be able to extract perfusion liquid 5 from the organ container 1 if the organ container 1 is in such an inclined position that the perfusion liquid 5 flows towards one of the edges. During pumping, the perfusion liquid 5 is pumped into the first liquid conduit 22, which conduit 22 is connected to the second liquid connection 65 of the membrane pump 4 and to the donor organ. The operation of the pump 4 will be further explained in the description of FIGS. 2 and 3.

The first liquid conduit 22 divides at branching point 89 into a first liquid supply 86 and a second liquid supply 87. The second liquid supply 87 contains a non-return valve 79 and a second buffer tank 88 for eliminating the pulsating liquid pressure of the perfusion liquid in the second liquid supply 87. Because of the non-return valve 79 the liquid in the buffer 88 can escape only via discharge 87. The first liquid supply 86 can be connected to an artery of a liver and the second liquid supply 87 can be connected to a vein of a liver which is not an artery. In this way, in the case of a liver, a pulsating and continuous perfusion liquid supply is achieved in the artery and the vein, respectively. In the situation where the donor organ to be transported is a kidney, the second liquid supply 87, including the second buffer tank 88, can be shut off at branching point 89 and disconnected. The first liquid supply 86 is then connected to the artery of the kidney.

For regulating the gas pressure and the throughput of the gas from the gas container 3 to the membrane pump 4, the device has a second valve 6 and a first valve 7 for reducing this gas pressure and for controlling the throughput of the gas, respectively. The second valve 6 and the first valve 7 are connected to the first gas conduit 20 between the gas container 3 and the membrane pump 4, the first valve 7 being located downstream of the second valve 6. The second valve 6 is designed, for example, to lower the pressure from about 1500 mbar to about 150 mbar.

For driving the membrane pump 4, gas under pressure is conducted into the membrane pump 4 through the first valve 7 via the inlet and outlet 64. Once the membrane pump 4 has been activated, the gas under pressure is conducted out of the membrane pump, through the first gas conduit 20 and via the pressure sensor 77 into the second gas conduit 21, by switching over the first valve 7. By repeating these actions a pulsating gas flow is produced. The second gas conduit 21 opens into the organ container 1. The organ container 1 is shut off by the second cover 90 in such a way that the gas conducted into it results in an overpressure in the organ container 1. Because of this there is less risk that dust and dirt end up in the organ container 1 and near the donor organ. The gas conduit 21 can also be directly connected to the organ so as to be able to pass gas through the organ.

For driving the membrane pump 4, gas under pressure is conducted into the membrane pump 4 through the first valve 7 via the inlet and outlet 64. Once the membrane pump 4 has been activated, the gas under pressure is conducted out of the membrane pump, through the first gas conduit 20 and via the second valve 2 into the second gas conduit 21, by switching over the first valve 7. By repeating these actions a pulsating gas flow is produced. The second gas conduit 21 opens into the organ container 1. The organ container 1 is shut off by the second cover 90 in such a way that the gas conducted into it results in an overpressure in the organ container 1. Because of this there is less risk that dust and dirt end up in the organ container 1 and near the donor organ. The gas conduit 21 can also be directly connected to the organ so as to be able to pass gas through the organ.

During organ perfusion it is of great importance that the pressure of the perfusion liquid 5 in the donor organ does not go above a specific value, because it can cause irreparable damage to the donor organ. The gas pressure in the first gas conduit 20 and the perfusion liquid pressure in the first liquid conduit 22 are measured by the first and second pressure sensors 8 and 9, respectively. The first pressure sensor 8 is connected to the first gas conduit 20 between the second valve 6 and the first valve 7 and the second pressure sensor 9 is connected to the first liquid conduit 22 downstream of the membrane pump 4.

Furthermore, the control means 10 are by a first communication connection 26 in contact with the second valve 6 for the control thereof, by a second communication connection 27 in contact with the first pressure sensor 8 and by a third communication connection 28 in contact with the second pressure sensor 9. On the basis of the information from the second pressure sensor 9, the pulsating flow of the gas to the membrane pump 4 can be regulated by actuating the first valve 7, in other words the perfusion liquid pressure generated by the membrane pump 4 can be controlled by controlling the throughput of the gas under pressure to this membrane pump 4, by means of control of the first valve 7.

With control means 10 it is also possible to arrange for a constant delivery of perfusion liquid 5 to be pumped to the donor organ. Because it is known how much perfusion liquid 5 the membrane pump 4 per pump cycle pumps, it is possible to determine how many pump cycles need to be produced per time unit to achieve a specific flow rate. The flow rate of a pump cycle of the membrane pump 4 is about 10 milliliter.

The pressure of the gas from the gas container 3 is about 1.5 bar. To prevent damage to the donor organ it is necessary to reduce the pressure in the first gas conduit 20 to a value of between 100 and 250 mbar. This reduction is produced by the second valve 6. For continuous control of the gas pressure, using the information from the first pressure sensor 8, the control means 10 control the second valve 6. The desired overpressure delivered by the pump 4 is between 20 and 80 mm Hg.

Furthermore, the control means 10 are in contact, via a fifth communication connection 30, with a sensor 12 winch is connected to the membrane pump 4. This sensor 12 registers when there is less than a specific quantity of perfusion liquid 5 in the membrane pump 4. If this is the case, the control means 10 stop the drive of the membrane pump 4 by blocking the supply of the gas to the membrane pump 4 with the first valve 7. This can become refilled with perfusion liquid by gravity.

The device further comprises an expansion tank or oxygenator 11, for keeping the gas pressure in the first gas conduit 20 constant, which is connected to the first gas conduit 20 via a third gas conduit 23 between the second valve 6 and the first valve 7. Part of the first liquid conduit 22 runs through the inside of the expansion tank 11 before reaching the donor organ. The expansion tank 11 can comprise a flexible container which is put under pressure by the gas. This part 78 of the first liquid conduit 20 consists of a tubular winding of fluid-tight material which is not gas-tight (semi-permeable). Because of this the perfusion liquid 5 can absorb the gas present in the expansion tank 11. If an oxygen-containing gas is used in the device as driving gas, the perfusion liquid 5 is in this way provided with extra oxygen. Perfusion with oxygen-rich perfusion liquid 5 has a very favourable effect on keeping the donor organ in good condition. After the perfusion of the donor organ, the perfusion liquid 5 flows into the organ container 1. In use the donor organ is supported on an organ support 80. The donor organ is in this case in direct contact with the perfusion liquid 5 in the organ container 1. The organ support consists of material which, while allowing the perfusion liquid to pass through, does not allow cell residues originating from the donor organ through. Because these cell residues are collected by the organ support 80, the perfusion liquid 5 remains of good quality. The organ support 80 is made of a sheet-like, flexible filter material in which the donor organ is, as it were, suspended during use. The organ support 80 is removable.

Figure 2:
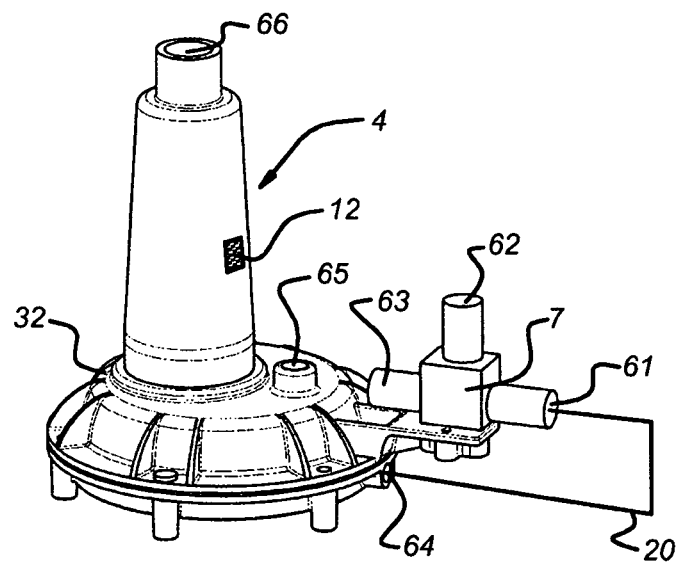
FIG. 2 shows a view in schematically perspective of the pump, including the valve, of the device in FIG. 1.

FIG. 2 shows an embodiment of the membrane pump 4 according to the invention. The first valve 7, which serves to actuate the membrane pump 4, is fixed to the housing 32 of the membrane pump 4. The first valve 7 has three connections, a first, second and third connection 61, 62 and 63, and can switch between two positions in which two of the three connections are in open connection with one another. The first connection 61 is connected by means of a gas conduit 20 to the inlet and outlet 64 of the gas part 33 of the membrane pump 4. The second and third connections 62 and 63 serve for the gas discharge and the gas supply, respectively. The first connection 61 is always in open connection with one of the two other connections 62 and 63.

The membrane pump 4 furthermore has a first and a second liquid connection 66 and 65. The first liquid connection 66 serves for the supply of liquid to the liquid part 34 of the membrane pump 4. The liquid is in this case first conducted through a liquid filter 47, after which the liquid flows into the reservoir 39 of the membrane pump 4. The liquid filter 47 takes impurities out of the liquid. The reservoir 39 is connected by means of a first one-way valve 40 to the liquid part 34 of the membrane pump 4. The second liquid connection 65 serves for the discharge of the liquid from the liquid part 34 and comprises a second one-way valve 41.

The gas part 33 is separated from the liquid part 34 by a membrane 44. In the rest position the first valve 7 is switched into a first position in which the first liquid connection 61 is in open connection with the second liquid connection 62, for the discharge of gas. For use, the liquid part 34 and, at least part of, the reservoir 39 must be filled with liquid. For driving the membrane pump 4, the first valve 7 is switched into the second position in which the first liquid connection 61 is in open connection with the third liquid connection 63, for the supply of gas. The gas under pressure will flow into the gas part 33, giving rise to an overpressure in this gas part 33. Because of this, the membrane 44 will move out of the rest position in such a way that the volume of the gas part 33 becomes greater. This results in an overpressure in the liquid part 34. Because of the first one-way valve 40, liquid from the reservoir 39 can only flow to the liquid part 34. The second one-way valve 41 permits only flows of liquid from the liquid part 34 through the second liquid connection 65 to the outside. Because of this, owing to the overpressure, liquid will be pumped out of the liquid part 34 via the second liquid connection 65.

After the membrane 44 has reached the maximum displacement thereof, the first valve 7 is switched into the first position. Because of the overpressure, gas will flow out of the gas part 33 through the first gas conduit 20. The membrane 44 will move in the direction of the rest position thereof, as a result of which an underpressure arises in the liquid part 34 relative to the reservoir 39 and the first one-way valve 40 will open. The result is that liquid flows from the reservoir 39 into the liquid part 34 until the pressures in the gas and liquid parts 33 and 34 are in equilibrium. The membrane pump 4 is then in the rest position again. By repeating the cycle described above, the membrane pump 4 can be used for pumping liquid. The first sensor 12 registers whether the reservoir is sufficiently full to guarantee that only perfusion liquid, and therefore no gas bubbles, are pumped.

The membrane pump 4 has the further advantage that in a pump cycle no underpressure occurs. This is of great importance for the quality of the donor organ, since in the event of an underpressure the blood vessels in the donor organ can suddenly close up and can become damaged.

Figure 3:
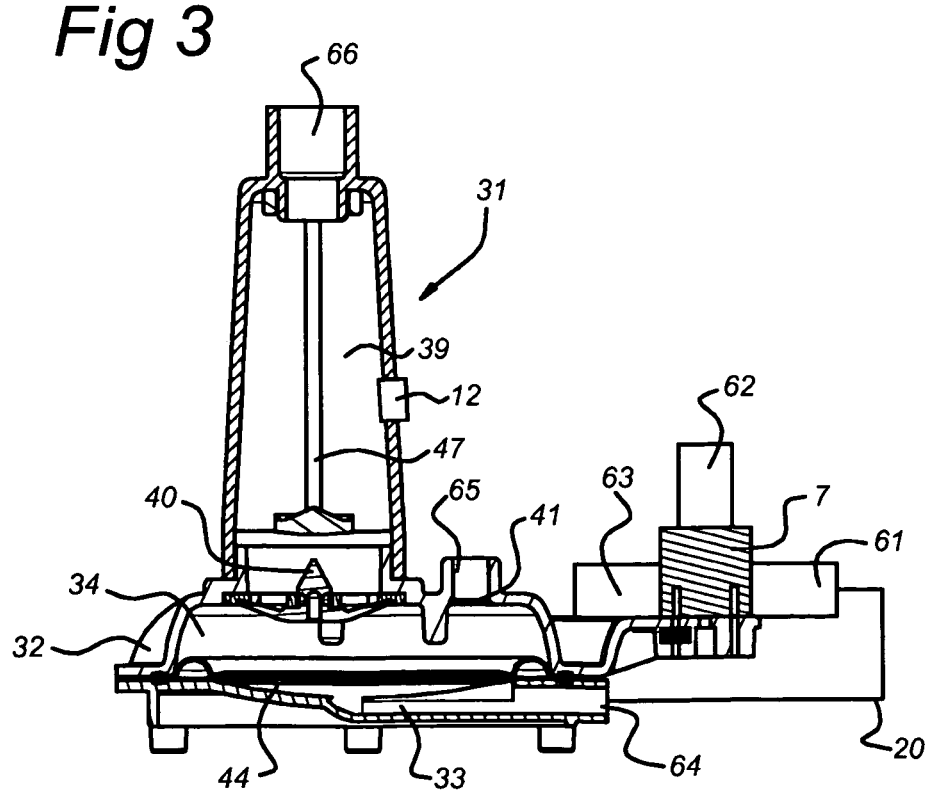
FIG. 3 shows a schematically cross-sectional view of the pump in FIG. 2.
Figure 4:
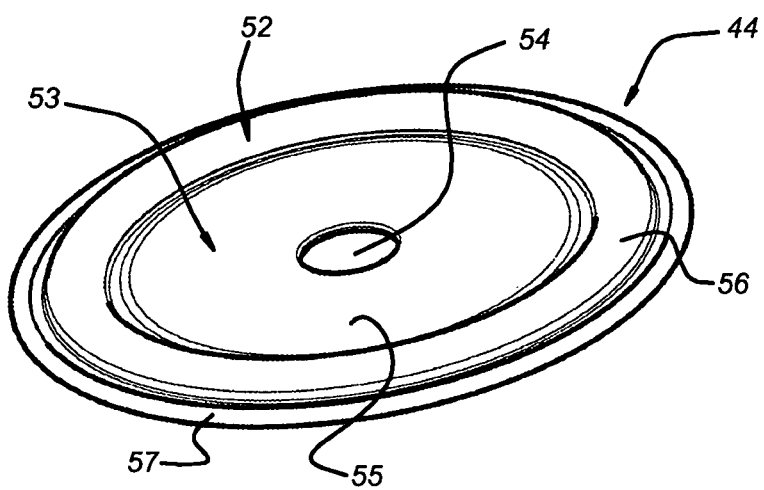
FIG. 4 shows a schematically perspective view of the membrane of the pump in FIG. 2.
Figure 5:
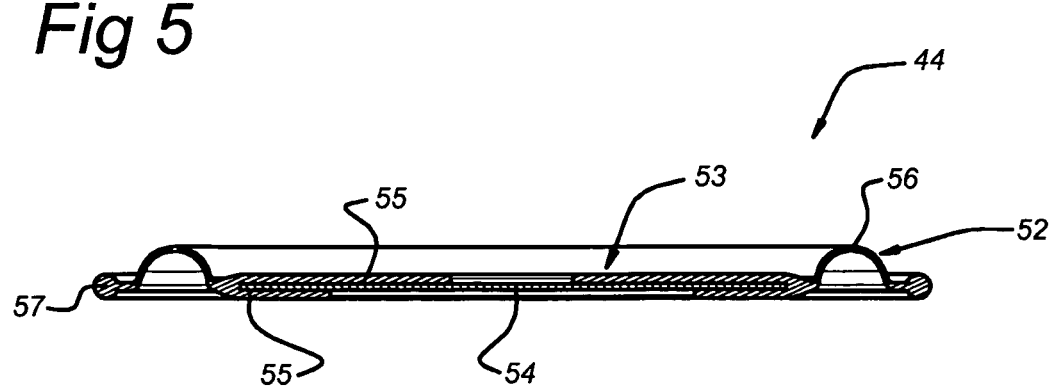
FIG. 5 shows a schematically cross-sectional view of the membrane in FIG. 4 and FIGS. 6a and 6b show views in perspective schematically of a subsequent embodiment of the device according to the invention.

FIGS. 4 and 5 show the membrane 44 of the membrane pump 4 in FIGS. 2 and 3. The membrane 44 is essentially circular. The membrane 44 is made of gas-tight material and comprises an outer edge 57, a flexible part 52 and a rigid inner part 53. The flexible part 52 surrounds the inner part 53 and the outer edge 57 surrounds the flexible part 52. The flexible part 52 has a fold 56 which extends outside the plane through the inner part 53. The inner part 53 comprises a rigid and an essentially circular member 54. This member 54 is partially covered on both sides thereof with a layer 55 which consists of the same material as the flexible part 52. This layer 55 is integrally joined to the flexible part 52. By providing the membrane 51 on one side thereof with an overpressure, the planes through the inner part 53 and the outer edge 57 will move relative to one another.

Figure 6A:
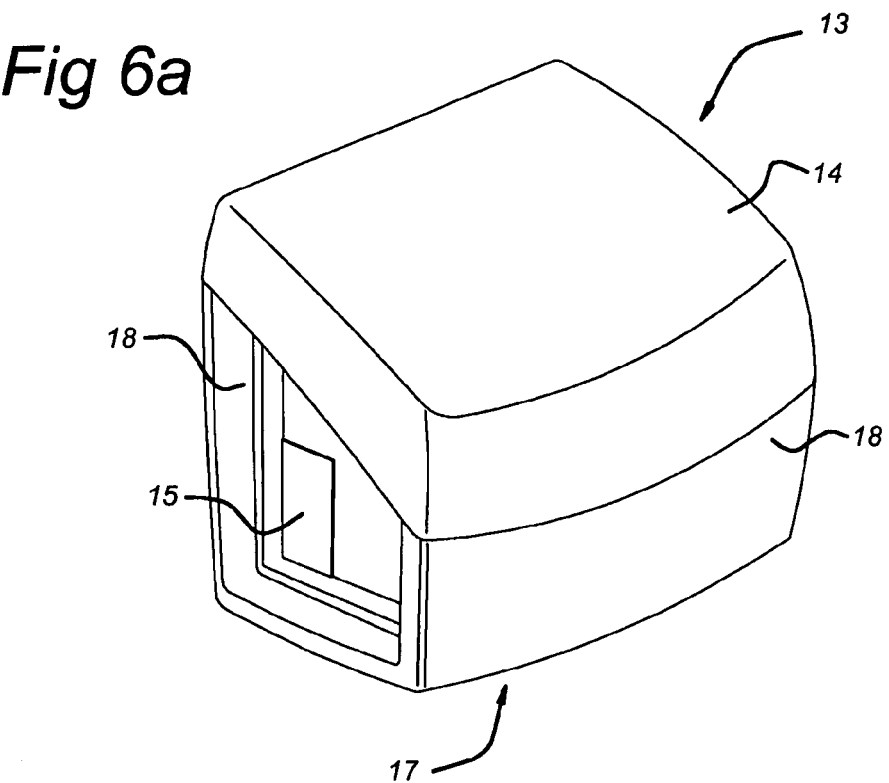

FIG. 6a shows a subsequent embodiment of a device according to the invention. The device has a housing 13 which comprises a first cover 14, side walls 18 and a base surface 17. In use the device is preferably positioned with the base surface 17 on a supporting surface. The housing 13 is essentially made of expanded polystyrene or tempex. Between the first cover 14 and the base surface 17 there is a closable opening 15 on the outer surface of the housing 13. Objects, such as the gas container 3 from FIG. 1 and cooling elements, can be placed in the housing 13 through this opening 15. The temperature in the organ container 101 is preferably between 2 and 8 degrees Celcius. The first cover 14 has such a shape that, owing to the weight of the device, it is in an unstable position when the device is positioned on a horizontal surface in such a way that only the first cover 14 is touching this surface. As a result of this the device will tilt to a position in which not just the first cover 14 touches the supporting surface and preferably to a position in which the base surface 17 is touching the supporting surface. The closable opening 15 can also be produced by a removable side wall 18.

Figure 6B:
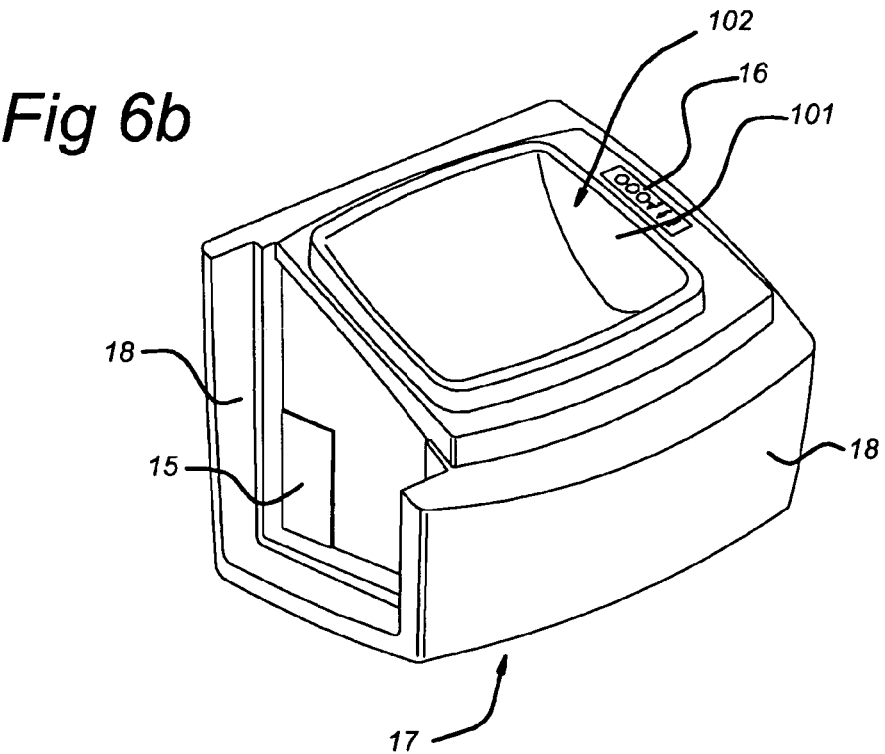

FIG. 6b shows the device in FIG. 6a where the first cover 14 and the second cover, not shown, of the organ container 101 have been removed. The plane through the periphery of the opening 102 of the organ container 101 is at an angle to the plane through the base surface 17. Owing to this positioning of the opening 102 of the organ container 101 it is easier to place a donor organ in the organ container 101.

Near the opening 102 are operating means 16 for controlling the organ perfusion process. With the operating means 16 it is possible to set what sort of organ, for example a kidney or a liver, will undergo the organ perfusion. Furthermore, parameters important for the organ perfusion, such as the desired pressure, the temperature and the flow rate can be set. During the perfusion process information that relates to these parameters is displayed by these operating means 16. In this way a view can be formed of the course of the organ perfusion during and after transport of the donor organ. This is of great importance for determining the quality of the donor organ after the transport phase.

The entire device, including the electronics, is resistant to ethylene oxide sterilisation. It will be clear to a person skilled in the art that within the extent of the scope of protection defined by the claims even further variants which are obvious after the above are conceivable.

The invention claimed is:

1. A device for transporting an organ, comprising:
    a) a container for organs,
    b) a gas-driven pump connected to said container by liquid conduits for circulating a liquid through said container,
    c) pressure sensor means provided in an output liquid conduit of the pump,
    d) an attachment for a gas bottle containing an oxygen-containing gas and a gas conduit connecting said gas bottle to said pump,
    e) a first valve provided in said gas conduit, wherein said first valve is connected to said pump via said gas conduit,
    f) a controller controlling said first valve for producing a pulsating gas flow of said oxygen-containing gas to said pump for operation thereof, and
    g) an oxygenator incorporated in said gas conduit between said gas bottle and said first valve,
    wherein said pressure sensor means are connected to said controller for controlling the drive of said pump, and
    wherein a part of the liquid conduits pass through an inside of the oxygenator, said part of the liquid conduits being semi-permeable so as to absorb oxygen from said oxygen-containing gas within said oxygenator into liquid to be circulated through said container.

2. The device according to claim 1, comprising a second valve provided in said gas conduit upstream of the first valve for controlling the pressure at said first valve.

3. The device according to claim 2, wherein said second valve is electrically adjustable and electrically connected to said controller.

4. The device according to claim 1, wherein said pump is a membrane pump.

5. The device according to claim 1, wherein said pump has a sensor for switching off said pump.

6. The device according to claim 1, having a housing with a base surface, side walls and a cover, dimensioned in such a way that, when said device is placed on said cover, said device tilts towards one of said side walls.

7. A method for transporting an organ in a container, comprising the steps of:
    a) placing an organ in a container,
    b) closing said container, and
    c) circulating a perfusion liquid through said container using a pump driven by pressure from an oxygen-containing gas from a gas bottle provided to said pump through a gas conduit connecting said pump to said gas bottle, the gas pressure on said pump being switched to obtain the pumping effect, the supply of gas to said pump being determined by the liquid pressure measured in the output conduit of said pump of said liquid generated by said pump, wherein said perfusion liquid is circulated through said container using liquid conduits, and wherein a part of said liquid conduits pass through an inside of an oxygenator incorporated in said gas conduit between said gas bottle and said pump, said part of the liquid conduits being semi-permeable so as to absorb oxygen from said oxygen-containing gas within said oxygenator into said perfusion liquid.

8. The method according to claim 7, comprising the step of supplying the oxygen-containing gas from a tank through said gas conduit to said pump, and supplying the perfusion liquid through a gas-permeable hose provided in said tank to said container.

9. A device for transporting an organ, comprising:
 a) a container for organs,
 b) a gas-driven pump connected to said container by liquid conduits for circulating a liquid through said container,
 c) an attachment for a gas bottle containing an oxygen-containing gas,
 d) a gas conduit connecting said gas bottle to said pump,
 e) a first valve provided in said first gas conduit, wherein said first valve is connected to said pump via said gas conduit,
 f) a controller controlling said first valve for producing a pulsating gas flow of said oxygen-containing gas to said pump for operation thereof, and
 g) an oxygenator incorporated in said first gas conduit, wherein said liquid conduits pass through said oxygenator so as to absorb oxygen from said oxygen-containing gas within said oxygenator into liquid to be circulated through said container.

10. The device according to claim 9, wherein a part of the liquid conduits pass through an inside of the oxygenator, said part being semi-permeable so as to absorb oxygen from oxygen-containing gas in said oxygenator into liquid to be circulated through said container.

11. The device according to claim 10, wherein said semi-permeable part is a part of an output liquid conduit of said pump.

12. The device according to claim 10, wherein said semi-permeable part consists of a tubular winding.

13. The device according to claim 9, wherein said device comprises pressure means provided in an output liquid conduit of the pump, said pressure means being connected to said controller for controlling the drive of said pump.

14. The device according to claim 9, wherein said first valve is adapted to switch between a first position and a second position, said first valve in the first position providing an open connection between said gas bottle and said pump, and said first valve in the second position providing an open connection between said pump and said container for organs through a second gas conduit connecting said first valve with said container for organs.

* * * * *